United States Patent [19]

Kaufhold et al.

[11] Patent Number: 4,579,992
[45] Date of Patent: Apr. 1, 1986

[54] PRODUCTION OF 3,3- AND 2,3-DIMETHYLBUTENES, 2,3-DIMETHYLBUTADIENE AND/OR GLYCOL OR POLYGLYCOL N-ALKYL-3,3- AND -2,3-DIMETHYLBUTYL ETHER

[75] Inventors: Manfred Kaufhold; Werner Smolka, both of Marl, Fed. Rep. of Germany

[73] Assignee: Huels Aktiengesellschaft, Marl, Fed. Rep. of Germany

[21] Appl. No.: 643,933

[22] Filed: Aug. 24, 1984

[30] Foreign Application Priority Data

Aug. 25, 1983 [DE] Fed. Rep. of Germany ....... 3330599
Mar. 2, 1984 [DE] Fed. Rep. of Germany ....... 3407756

[51] Int. Cl.$^4$ ................................................ C07C 1/26
[52] U.S. Cl. .................................... 585/612; 585/641; 585/642
[58] Field of Search .................. 585/612, 641, 642

[56] References Cited

U.S. PATENT DOCUMENTS 2,322,258  6/1943  Strosacker et al. ................. 585/642

FOREIGN PATENT DOCUMENTS 632193  5/1963  Belgium ............................. 585/612

Primary Examiner—Curtis R. Davis
Attorney, Agent, or Firm—Millen & White

[57] ABSTRACT

For the production of 3,3- and 2,3-dimethylbutene, respectively, and 2,3-dimethylbutadiene and/or for the simultaneous production of 3,3- and 2,3-dimethylbutene, respectively, 2,3-dimethylbutadiene, and glycol or polyglycol n-alkyl-3,3- and -2,3-dimethylbutyl ether, respectively, alkali hydroxides are reacted in a two-phase liquid system in the presence of a glycol or polyglycol ether, respectively, at temperatures of 100°–250° C., with mono- and dichlorodimethylbutane, respectively. By using, as the glycol or polyglycol ether, a glycol or polyglycol monoalkyl ether, the glycol or polyglycol n-alkyl-3,3- and -2,3-dimethylbutyl ether, respectively, is obtained besides the olefin.

26 Claims, No Drawings

PRODUCTION OF 3,3- AND 2,3-DIMETHYLBUTENES, 2,3-DIMETHYLBUTADIENE AND/OR GLYCOL OR POLYGLYCOL N-ALKYL-3,3- AND -2,3-DIMETHYLBUTYL ETHER

BACKGROUND OF THE INVENTION

This invention relates to the production of dimethyl substituted $C_4$ olefins and to special dialkyl glycol ethers.

Syntheses of 3,3-dimethylbutene-1 (neohexene) from 1-chloro-3,3-dimethylbutane (neohexyl chloride) are described in the literature, such as, for example, in German Pat. No. 1,253,700, suggesting a thermal dehydrochlorination at 350°–800° C. (500°–700° C.) and brief residence times in the absence of catalysts. This process is expensive owing to the high temperatures and the problems associated with the resultant, corrosive hydrogen chloride by-product. In addition, the residence time must be very accurately controlled to avoid the formation of major amounts of 2,3-dimethylbutene-1 and 2,3-dimethylbutene-2 due to rearrangement of 3,3-dimethylbutene-1 (neohexene).

Sodatova et al (see Chemical Abstr. 79: 41796 [1973]) propose the reaction of 1-chloro-3,3-dimethylbutane (neohexyl chloride) with potassium acetate in the presence of acetic acid at 180°–200° C., and under 22 atmospheres to obtain the corresponding acetic acid ester, and splitting the latter thermally at 500° C. to obtain the 3,3-dimethylbutene-1 (neohexene) and acetic acid. This two-stage process likewise requires high temperatures and can be performed only in a pressurized apparatus.

In contrast thereto, A. Brändström [see Acta Chem. Scand. 13: 611–612 (1959)] describes a laboratory method for the dehydrochlorination of neohexyl chloride operating in a single stage at relatively low temperatures, 120°–190° C., with potassium hydroxide as the alkali and polyethylene glycol as the solvent. In this process, a homogeneous mixture is obtained with the aid of the polyethylene glycol employed. However, one drawback in this connection is that the thus-produced potassium chloride cannot be removed in an industrially simple way, e.g., by a water scrubbing step, without wastewater problems. In addition, the yield is low.

Also, syntheses of 2,3-dimethylbutene-1 and 2,3-dimethylbutene-2 have been described in the literature, such as, for example, in DAS No. 2,917,779 proposing a three-stage synthesis, starting with isovaleraldehyde. In this process, isovaleraldehyde is reacted with formaldehyde to the α-isopropylacrolein, this unsaturated aldehyde is subsequently hydrogenated to 2,3-dimethylbutanol, and the dehydration conducted thereafter yields a mixture of the isomeric olefins 2,3-dimethylbutene-1 and 2,3-dimethylbutene-2. This process requires relatively expensive chemicals and is industrially expensive because it requires many stages. Despite these disadvantages, this process, as explained in detail in the specification of DAS No. 2,917,779, is an improvement over the processes heretofore known in the literature for the dimerization of propene wherein the methylpentenes, which are difficult to separate, are always obtained as the by-product.

Besides this process, the selective hydrogenation of 2,3-dimethylbutadiene has also been suggested for the preparation of 2,3-dimethylbutene-2. This starting material is, however, difficult to obtain and thus this process is of little industrial interest.

In contrast, more interesting are methods starting with the readily accessible 2,3-dimethylbutane. This hydrocarbon is formed in the production of the musk fragrance 7-acetyl-1,1,3,4,4,6-hexamethyl-1,2,3,4-tetrahydropnaphthalene (so-called acetyl-HMT, German Pat. No. 2,457,550) as a by-product, namely at a certain stage of this synthesis, in the reaction of p-cymene with 3,3-dimethylbutene-1 (neohexene) or with 2,3-dimethylbutene-1 in equimolar amounts (DAS No. 1,035,826). The mechanism behind this interesting reaction has been described in detail by T. F. Wood and J. Angioloni in "Tetrahedron Letters" 1: 1-8 (1963).

Conversion of 2,3-dimethylbutane into the olefin mixture is possible, for example, by dehydrogenation or by chlorination and subsequent dehydrochlorination. The dehydrogenation, investigated by L. B. Fisher, M. P. Terpugova, and I. L. Kotlyarevskii [Izvest. Vostoch Filial, Akad. Nauk, SSSR 1957, No. 9.53-6; or Chem. Abstr. (1958): 12746], has the disadvantage that high temperatures of about 550° C. are required, and that 2,3-diemthylbutadiene is formed as a by-product. Separation of the diene and the unreacted 2,3-dimethylbutane from the monoolefin mixture is, however, very expensive on account of their very close boiling points.

This drawback is eliminated by choosing a method wherein 1-chloro-2,3-dimethylbutane and/or 2-chloro-2,3-dimethylbutane occur as the by-products since these have a considerably higher boiling point than 2,3-dimethylbutane. The production of a mixture of this chlorine compound is simple to carry out industrially by chlorination of 2,3-dimethylbutane. However, higher-chlorinated products are also formed in minor amounts in this process. The actual problem, though, resides in the subsequent dehydrochlorination since the two isomeric monochlorine compounds show very different stabilities. According to Vives, V. C.; Kruse, C. W.; and Kleinschmidt, R. F. (Ind. Engng. Chem., Product Res. Development 8 [1969] 4: 432–435), 2-chloro-2,3-dimethylbutane, as a tertiary chlorine compound, is dehydrochlorinated readily at its boiling point (bp=112° C.) with a large number of catalysts, whereas the primary chlorine compound, 1-chloro-2,3-dimethylbutane, requires temperatures of about 300° C. for dehydrochlorination. For this reason, these authors propose the use of tertbutyl chloride as the chlorinating agent because only the tertiary chlorine compound is produced. Isobutane is formed from the tertiary butyl chloride, namely in equimolar amounts as a waste product.

The process is therefore expensive because of its high consumption of chemicals. In the thus-produced olefin mixture, the ratio of isomers of α-olefin/β-olefin is 1:3.

In order to obtain extensive dehydrochlorination of the mixture of primary and tertiary chlorine compounds, U.S. Pat. No. 2,613,233 proposes to effect a two-stage splitting step wherein, in the first stage, temperatures are set at 120°–130° C. and, in the second stage, at 500°–600° C. This process thus is likewise relatively expensive and requires costly reactors of special steels on account of the high temperatures.

All of the conventional methods accordingly demand high temperatures, expensive technical apparatus, or costly chemicals, can be carried out only in several stages, or create problems in waste disposal.

SUMMARY

Accordingly, an object of this invention is to provide a process wherein a simple dehydrochlorination without the need for costly chemicals can be performed on 1-chloro-3,3-dimethylbutane (neohexyl chloride) readily accessible by reaction of tert-butyl chloride with ethylene, and/or on the mixture of the monochlorides readily accessible by chlorination of 2,3-dimethylbutane, as well as on the dichlorinated products obtained as the by-product.

Another object is to provide a process, according to which it is possible, with low technical expenditure, to produce 3,3-dimethylbutene-1 and/or a mixture of 2,3-dimethylbutene-1 and 2,3-dimethylbutene-2, from the inexpensive 1-chloro-3,3-dimethylbutane (neohexyl chloride) and the inexpensive monochlorination products of 2,3-dimethylbutane, from 2-chloro-2,3-dimethylbutane, and from 1-chloro-2,3-dimethylbutane, and which makes it possible to likewise dehydrochlorinate the higher-chlorinated products of 2,3-dimethylbutane, i.e. primarily the isomeric dichloro-2,3-dimethylbutanes and to transfer the resultant reaction products to further uses.

Still another object is to provide novel dialkyl ethers especially those which can be produced in conjunction with the dimethyl substituted olefins.

Upon further study of the specification and appended claims, further objects and advantages of this invention will become apparent to those skilled in the art.

To attain these objects, according to one aspect of this invention, there is provided a process for the production of 3,3-dimethylbutene-1 (=neohexene), 2,3-dimethylbutene-1, and 2,3-dimethylbutene-2 or of 2,3-dimethylbutadiene and/or for the simultaneous production of these olefins and glycol or polyglycol n-alkyl-3,3- and -2,3-dimethylbutyl esters, respectively, of Formula 1 ($R_2$=3,3- and 2,3-dimethylbutyl, respectively), by dehydrochlorination of 1-chloro-3,3-dimethylbutane and 1-chloro-2,3-dimethylbutane, respectively, individually or in a mixture with 2-chloro-2,3-dimethylbutane or dichloro-2,3-dimethylbutane, respectively, with alkali hydroxides in the presence of glycol and polyglycol ethers, respectively, of general Formula 1 and/or 2. By using the glycol or polyglycol monoalkyl ethers of general Formula 2 as the glycol or polyglycol ethers, the glycol or polyglycol dialkyl ether of Formula 1 wherein $R_2$ is the 3,3- and 2,3-dimethylbutyl residue, respectively, is simultaneously obtained in addition to the 3,3-dimethylbutene and/or the 2,3-dimethylbutenes.

| $R_1(OCH_2CH_2)_nOR_2$ FORMULA 1 | $R_1(OCH_2CH_2)_nOH$ FORMULA 2 |
|---|---|
| $R_1$ = n-butyl<br>n-hexyl<br>n-octyl<br>2-ethylhexyl | n = 1, 2, 3<br>$R_2$ = tert-butyl<br>3,3-dimethylbutyl or<br>2,3-dimethylbutyl. |

According to another aspect of the invention, there is provided in the dehydrochlorination of at least one of 1-chloro-3,3-dimethylbutane, 2-chloro-2,3-dimethylbutane, 1-chloro-2,3-dimethylbutane and dichloro-2,3-dimethylbutane, the improvement comprising conducting said dehydrochlorination in the presence of a glycol and/or polyglycol ether of the Formula 1 and/or 2.

Surprisingly, 3,3-dimethylbutene-1 (neohexene) is obtained in a high purity (above 98%) and/or a mixture of 2,3-dimethylbutene-1 and 2,3-dimethylbutene-2 is obtained with a purity of above 98% (determined, for example, by gas chromatography), in a ratio of isomers of $\alpha$-:$\beta$-olefin of about 14:3, and in good yields, by providing solid alkali hydroxide and a glycol or polyglycol ether; heating to 100°–250° C., preferably 120°–200° C., especially 150°–180° C.; adding the monochlorides of 3,3- and 2,3-dimethylbutane-1 and/or the mixture of the monochlorides of 2,3-dimethylbutane (denoted hereinbelow as monochloride mixture); and removing by distillation over a column the thus-formed low-boiling compounds and water and unreacted chlorine compounds. The reaction generally takes place within a time period of 2–10 hours.

Preferred alkali hydroxides are sodium or potassium hydroxide as well as their mixtures. The molar ratio of alkali:chlorine compound is ordinarily 1:1 to 1:5, preferably 1:1 to 1:2.

Suitable glycol or polyglycol ethers are glycol or polyglycol dialkyl ethers of Formula 1, for example glycol n-butyl-3,3- and -2,3-dimethylbutyl ether, diglycol n-butyl-3,3- and -2,3-dimethylbutyl ether, diglycol n-butyl-tert-butyl ether, triglycol n-butyl-3,3- and -2,3-dimethylbutyl ether, etc., as well as glycol or polyglycol monoalkyl ethers of Formula 2, for example n-butyl glycol, n-hexyl glycol, n-octyl glycol, 2-ethylhexyl glycol, n-butyl diglycol, n-hexyl diglycol, n-octyl diglycol, 2-ethylhexyl diglycol, n-butyl triglycol, n-hexyl triglycol, n-octyl triglycol, 2-ethylhexyl triglycol.

The glycol or polyglycol ethers are generally utilized in amounts from 0.1 to 1 mole/mole of chlorine compound, preferably 0.25–0.5 mol/mol.

When using the glycol or polyglycol mono-n-butyl ethers and/or the glycol or polyglycol n-butyl-3,3- or -2,3-dimethylbutyl ethers, the reaction takes place preferably at temperatures of 150°–250° C., especially 200°–220° C.

Especially sutiable as the glycol or polyglycol ethers are those not readily soluble in water and/or aqueous alkali chloride solution, so that the alkali chlorides formed as the by-product can be removed by washing with water, and the wastewater has a low carbon content. It was found surprisingly that these relatively insoluble nonpolar solvents make possible the reaction between the alkali hydroxide and the monochloride mixture. In general, the glycol or polyglycol ethers employed in this invention are soluble in water to the extent of not more than 50 g/l, especially not more than 0.5 g/l at 20° C. This is to be contrasted to the polyethylene glycol used by Brändström which is soluble in water in each ratio.

The two phase liquid system comprises butyl diglycol, the corresponding neohexyl ether and the aqueous alkali chloride solution. The two phase liquid system renders possible to wash out the alkali chloride with water after cooling. This washing is not possible by Brändström, because there is no separation of phase.

A polyglycol dialkyl ether especially suitable for this process is, for example, the diglycol n-butyl-tert-butyl ether which is technically accessible by reaction of n-butyl diglycol with isobutylene.

It was found surprisingly that a solvent suitable for the process of this invention is produced in the process proper by initially employing a glycol or polyglycol monoalkyl ether of Formula 2 as the solvent and/or suspension agent. The process can in this case be conducted in two stages and yields, in both stages, 3,3- dimethylbutene-1 and the 2,3-dimethylbutenes, respectively, and in the first stage, produces the ether suitable for the second stage as the solvent or suspension medium. In this connection if the corresponding ether, for example, the diglycol n-butyl-neohexylether is produced, this ether is used as aid for the solution between alkali hydroxides and the 3,3- or 2,3-Dimethyl-chlorobutane.

Although many different compounds according to Formula 2 can be used for this process as the glycol or polyglycol monoalkyl ethers, for example the above-mentioned ethylene oxide adducts, preferred for economic reasons are the reaction products of n-butanol with ethylene oxide, readily available commercially, i.e. the following compounds:
  n-butyl glycol
  n-butyl diglycol
  n-butyl triglycol.

The use of these glycol ethers offers, inter alia, the following advantages:

1. Despite their high solubility in water, the wastewater evolving from the process of this invention contains relatively little carbon compound.

2. The ethers of the type of Formula 1 with $R_2$=3,3- or 2,3-dimethylbutyl, obtained in the first stage, are obtained in the pure form by a simple distillation processing step, and are suitable for the second stage of the process.

3. The ethers mentioned in (2) are more stable thermally and against acids than the aforementioned corresponding tert-butyl ethers, so that only mechanical losses of suspension agents occur in the process.

These results are surprising in their extent and demonstrate the simple way in which the process can be carried out industrially. The ethers of Formula 1 with $R_2$=3,3- or 2,3-dimethylbutyl are novel.

The following novel dialkyl ethers are especially suitable in this connection: glycol n-butyl-3,3- and -2,3-dimethylbutyl ether, respectively; diglycol n-butyl-3,3- and -2,3-dimethylbutyl ether, respectively; triglycol n-butyl-3,3- and -2,3-dimethylbutyl ether, respectively. Based on their surprisingly high stability, they are also suitable for other uses, such as, for example, as brake and hydraulic fluids, coolants and heating media, lubricants, selective adsorbents for acid gases, and so forth.

Another advantage of this process resides in that it is also feasible to dehydrochlorinate the higher-chlorinated products of 2,3-dimethylbutane, especially dichloro-2,3-dimethylbutane, so that they need not be destroyed by expensive methods, such as, for example, by combustion. The low-boiling cleavage product formed is 2,3-dimethylbutadiene, representing a valuable starting material for other syntheses.

Also the above-mentioned high ratio of the 2,3-dimethylbutenes is advantageous because in this way 2,3-dimethylbutene-1 is accessible in large amounts in an economical fashion.

This olefin is a suitable reactant with p-cymene in the manufacture of the above-mentioned must fragrance acetyl-HMT (DAS No. 1,593,653) so that, via this procedure, the 2,3-dimethylbutane formed as the by-product can be returned into the production of acetyl-HMT.

The process of this invention is conducted, for example, as follows:

Starting products for the process of this invention are 1-chloro-3,3-dimethylbutane, generally produced from tert-butyl chloride and ethylene with aluminum chloride as the catalyst at low temperatures, −15° to −30° C. (Schmerling, J. Amer. Chem. Soc. 67: 1152 [1945]), and chlorinated 2,3-dimethylbutanes, respectively, obtained in the usual way with or without a catalyst at a somewhat elevated temperature, e.g., at 50° C., by chlorination of 2,3-dimethylbutane, hydrogen being substituted by chlorine (Houben Weyl, "Methoden der organischen Chemie" [Methods of Organic Chemistry] vol. V/3, "Halogen Counpounds" [1962] pp. 571 et seq., 4th ed. Georg Thieme Publishers, Stuttgard). The chlorination product is divided by distillation into two fractions: The first fraction is unreacted 2,3-dimethylbutane which is recycled into the chlorination. The second fraction is the desired monochloride mixture, 2-chloro-2,3-dimethylbutane, and 1-chloro-2,3-dimethylbutane obtained in a ratio of 35:65 to about 40:60. The distillation residue contains the higher-chlorinated products; as espected, the dichlorides predominate. The monochloro and the dichloro compounds are used separately in the dehydrochlorination stages, namely in the following way:

Alkali metal hydroxide, for example solid sodium hydroxide or potassium hydroxide, or mixtures of these alkalis, and an n-butyl glycol or polyglycol monoether are charged into a conventional stirred apparatus on which a distillation column has been mounted, heated under agitation to 100°–250° C., preferably 150°–180° C., thus forming two liquid phases comprising the lower heavy phase with the alkali hydroxides and tiny amounts of dissolved glycol compounds and the upper phase with the starting glycol compounds and tiny amounts of dissolved alkali hydroxide. The monochloride mixture or the dichloride mixture is gradually added. Temperatures higher than 250° C. should be avoided since this would present danger of decomposition of the butyl glycol ether. At temperatures of below 150° C., the reaction proceeds sluggishly.

When a portion of the chlorine compound is added, the formation of fine alkali chloride crystals is observed, and the corresponding unsaturated compound is obtained at about 40° C. to 85° C. at the head of the column. After some time, the head temperature rises to 80°–100° C., and at this point in time relatively large amounts of water are found in the distillation receiver. This means that the water formed by the reaction combines with the olefins and the chorine compounds to form binary minimum boiling azetropes which can be easily distilled.

Toward the end, the head temperature increases, depending on the molar ratio of alkali to chlorine compound employed, up to the boiling temperature of the starting material, for example, 117° C. in case of 1-chloro-3,3-dimethylbutane, which means the reaction has been completed. The molar ratio of alkali:chlorine compound is suitably selected to be 1:1 to 1:5, preferably 1:1 to 1:2. Since the unreacted alkali is not recovered, it is not advantageous to employ the chlorine compound in less than stoichiometric amounts.

When there is no longer any distillate being produced, the mixture is cooled under agitation and then the finely suspended alkali chloride is washed out with water.

The sump product is stirred with so much water, that the alkali chlorides are dissolved and a quite saturated aqueous solution is formed. Then the phases are separated and the aqueous solution is rejected.

The oil phase is distilled thus obtaining n-butyl glycol and polyglycol monoether, respectively, and the corresponding glycol n-butyl and/or polyglycol n-butyl-3,3- and -2,3-dimethylbutyl ethers.

The thus-produced ether can be utilized in the second stage as suspension agent for alkali. The second stage is conducted analogously to the first stage. The high stability of the ethers permits the use of higher temperatures, preferably 150°–250° C., especially 200°–220° C. Thus, on a technical scale, it would be preferred to use dialkyl ethers, preferably on a continous basis with the regenerated ether being recycled to a reaction step.

The water is separated from the two-phase distillates of the first and second stages and discarded. The redistillation of the oil phase yields the monoolefins in a purity of above 99% and 2,3-dimethylbutadiene in a purity of more than 97%.

3,3-Dimethylbutene-1 and 2,3-dimethylbutene-1, produced according to this invention, are suitable for manufacturing acetyl-HMT [a musk fragrance, 7-acetyl-1,1,3,4,4,6-hexamethyl-1,2,3,4-tetrahydronaphthalene, also called "Tonalid" or "Veritone" (see German Pat. No. 2,457,550)] and furthermore are valuable intermediates for numerous other industrial syntheses. This also holds true for the thus-produced 2,3-dimethylbutene-2 and 2,3-dimethylbutadiene. For example, 2,3-dimethylbutene-2 is a important starting product for the production of Pinacol, 2,3-dimethyl-butane (see EP-Pat. No. 0 010 236), which for example is used as odoriferous substance or as starting product for Pinacolon. 2,3-Dimethylbutadiene is used for the production of the so called methyl-rubber (see Ullmanns Encyklopädie der technischen Chemie, Vol. 10, Kohlenwasserstoffe, p. 68; Urban & Schwarzenberg (1958).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A glass apparatus is used consisting of a four-necked flask with agitator, thermometer, and a distillation column with distillation attachment.

The following materials are used:
336.6 g diethylene glycol n-butyl-tert-butyl ether (=DGBB)
112.2 g (1.8 mole) potassium hydroxide, industrial quality (about 90% strength)
492.3 g (4 moles) 1-chloro-3,3-dimethylbutane (neohexyl chloride), 98% strength Diethylene glycol n-butyl-tert-butyl ether and potassium hydroxide are charged into the reactor and heated under agitation and a nitrogen atmosphere to 220° C., thus producing two liquid phases. Within 6.5 hours, neohexyl chloride is then added dropwise. After the addition of about 30 ml of the chlorine compound, a distillate is obtained at 39°–40° C. The ratio of reflux to discharge is first set at 5:1 and after one-half hour at 3:1. At this reflux ratio, the head temperature rises, and then water is concomitantly distilled over until, after 7¼ hours, the boiling temperature of neohexyl chloride (117° C.) has been reached. After 8¼ hours, the first fraction is complete. The sump product is cooled to 160° C. and, under further agitation, distillation fraction 2 is obtained at 133 mbar. The amounts are set forth in the table below:

| Fract. No. | Temperature (°C.) Sump | Temperature (°C.) Head | Weight (g) | Pressure (mbar) | Ratio of Reflux to Discharge |
|---|---|---|---|---|---|
| 1 | 220 | 39–117 | 469 | normal | 5:1 |
| Cooling Trap to 1st Fract. | | 114 | 6 | | 3:1 |
| 2 | 160–168 | 54–150 | 38 | 133 | 3:1 |
| Cooling Trap to 2nd Fract. | | | 12 | | |
| Residue | | | 429 | | |
| | | | 954 | | |

Fractions 1 and 2 are combined with the corresponding cooling traps and 35 g of water is separated in case of the first fraction. The most important components of these two mixtures, determined by gas chromatography, are listed in the following table:

| | Neo hexene | Neo hexyl Chloride | Neo- hexanol | Dineohexyl Ether | DGBB |
|---|---|---|---|---|---|
| Fraction 1 and Cooling Trap | 24.1 | 64.4 | 2.2 | — | — |
| Fraction 2 and Cooling Trap | 0.7 | 15.3 | 3.2 | 20.1 | 36.6 |
| Sump Phase | — | — | — | — | 91.8 |

The sump product is stirred with 450 g of water and then the phases are separated: oil phase 286 g (GC analysis see above), aqueous phase 569 g with 4.66% potassium hydroxide and a carbon content of 0.5%.

From the above-mentioned figures, the conversion of neohexyl chloride is calculated to be about 40%. The neohexene yield, based on converted neohexyl chloride, is about 80 molar percent. Two valuable by-products, neohexanol and dineohexyl ether, are produced in yields of 6.9 mol-% and 3.1 mol-%, respectively, based on reacted neohexyl chloride.

The neohexene-containing fractions are combined and redistilled. This distillation yields neohexene with 98.5% purity according to analysis by gas chromatography.

EXAMPLE 2

The procedure of Example 1 is followed; instead of using potassium hydroxide, 1 mole of potassium hydroxide and 1 mole of sodium hydroxide is utilized, as well as 2 moles of neohexyl chloride. A conversion of about 50% is attained in this procedure. The yields of neohexene, neohexanol, and dineohexyl ether, based on converted neohexyl chloride, are 70.0 mol-%, 6.1 mol-%, and 7.1 mol-%, respectively.

EXAMPLE 3

The process is conducted as described in Example 1; n-butyl diglycol is used in place in DGBB:
259.5 g (=2.13 moles) neohexyl chloride (99.0% strength)
112.2 g (=1.8 moles) potassium hydroxide, technical grade (about 90% strength)

336.6 g n-butyl diglycol (98.6% strength)

The reaction temperature is set at 170° C. Here again, two liquid, readily stirrable phases are formed.

The carbon content of the wastewater is 1.3% and is reduced to 0.7% by twice washing with neohexyl chloride.

The oil phase obtained after reaction and the water scrubbing step exhibits the following composition:
n-butyl diglycol: 47.1%
diglycol n-butylneohexyl ether: 50.4%
high-boiling compounds: 2.5%

The conversion of neohexyl chloride is 77.7%. The yields, based on unreacted neohexyl chloride, are as follows:
neohexene: 52.7 mol-%
neohexanol: 6.5 mol-%
dineohexyl ether: 0.1 mol-%
diglycol n-butyl- neohexyl ether: 34.2 mol-% (=DGBN)

By distillation, DBGN with a boiling point of 145°–150° C. is separated at 13 mbar from n-butyl diglycol and obtained with a purity of 99.6%.

The H-NMR spectrum of this novel ether shows three different groups of signals, corresponding to the types of protons denoted in the structure with a, b, and c:

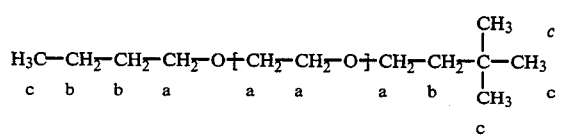

a-proton signal at 3.5 ppm
b-proton signal at 1.5 ppm
c-proton signal at 0.9 ppm
measured in carbon tetrachloride against tetramethylsilane as the standard.

Density: $d^{20}/4 = 0.8751$
Index of refraction: $n_D^{20} = 1.4268$
IR Bands: 740 cm$^{-1}$ (n-butyl group), 1,120–1,125 cm$^{-1}$ (R—O—R—group)

EXAMPLE 4

The process is conducted as described in Example 3, but using n-butyl triglycol instead of n-butyl diglycol. The following results are obtained:

The carbon content of the wastewater is 1.7% and is lowered by a one-time scrubbing step with neohexyl chloride to 1.3%.

The neohexyl chloride conversion is 73%. The yields of valuable products, based on converted neohexyl chloride, are:
neohexene: 61.0 mol-%
neohexanol: 2.4 mol-%
triglycol n-butyl- neohexyl ether: 33.2 mol-%

Also this novel ether, the boiling point of which at 13 mbar is about 174° C., is purified by distillation.

The position of the proton signals in the H-NMR spectrum coincides satisfactorily with the spectrum of DGBN.

Density: $d^{20}/4 = 0.9102$
Index of refraction: $n_D^{20} = 1.4331$
IR Bands: 740 cm$^{-1}$ (n-butyl group), 1,120–1,125 cm$^{-1}$ (R—O—R—group)

EXAMPLE 5

The process is carried out as set forth in Example 3, only employing n-butyl glycol in place of n-butyl diglycol. On account of the relatively low boiling point, the lowermost part of the distillation column is air-cooled. Similar results are obtained as in Examples 3 and 4. The resultant novel glycol n-butylneohexyl ether has, at 13 mbar, a boiling point of about 92° C. and is obtained by distillation in more than 99% purity.

The position of the proton signals in the H-NMR spectrum of this ether satisfactorily coincides with the spectrum of DGBN.

Density: $d^{20}/4 = 0.8331$
Index of refraction: $n_D^{20} = 1.4187$
IR Bands: 740 cm$^{-1}$ (n-butyl group), 1,120–1,125 cm$^{-1}$ (R—O—R—group)

EXAMPLE 6

The apparatus of Example 1 is utilized, the starting materials being:
243 g (=2 moles) neohexyl chloride (99.2% strength)
112.2 g (=1.8 moles) potassium hydroxide, technical grade (about 90% strength)
336.6 g diglycol n-butylneohexyl ether (=DGBN)

DGBN and potassium hydroxide are provided in the reactor and heated to 200° C. under agitation and a nitrogen atmosphere. Starting with about 150° C., two liquid, readily stirrable phases are formed. The further conductance of the process and the working-up operation take place as disclosed in Example 1.

The following result is obtained:
The carbon content of the wastewater is 1.2%.
Conversion of neohexyl chloride: 65%
Yields, based on converted neohexyl chloride:
    neohexene: 71.3 mol-%
    neohexanol: 8.7 mol-%
    dineohexyl ether: 6.9 mol-%

EXAMPLE 7

The process is conducted as in Example 6, but adding 20 g of n-butyl diglycol to the neohexyl chloride. The thus-formed water has a carbon content of 0.38%.

The following result evolves:
Conversion of neohexyl chloride: 51.0%
Yields, based on converted neohexyl chloride:
    neohexene: 81.3 mol-%
    neohexanol: 5.8 mol-%
    dineohexyl ether: 1.7 mol-%
    DGBN: 8.0 mol-%

If mechanical losses of DGBN occur in an industrial plant, these can be compensated for in this way by new formation of DGBN.

EXAMPLE 8

The process is conducted as in Example 6, by raising the temperature from 200° to 220° C. and the amount of neohexyl chloride from 2.0 to 2.5 moles.
Result:
The carbon content of the wastewater is 0.54%.
Conversion of neohexyl chloride: 60.0%
Yields, based on converted neohexyl chloride:
    neohexene: 64.2 mol-%
    neohexanol: 10.0 mol-%
    dineohexyl ether: 8.8 mol-%

EXAMPLE 9

The process is carried out as described in Example 8, but raising the temperature from 220° C. to 250° C. The following result is obtained:

The carbon content in the wastewater is 1.4%.

The distillation residue contains about 0.8% of n-butyl diglycol, formed by decomposition of DGBN.

Conversion of neohexyl chloride: 40.0%

Yields, based on converted neohexyl chloride:
- neohexene: 73.8 mol-%
- neohexanol: 20.2 mol-%
- dineohexyl ether: 3.4 mol-%

EXAMPLE 10

A glass apparatus is used consisting of a four-necked flask with agitator, thermometer, and a distillation column with distillation attachment.

The following starting materials are employed:
336.6 g diethylene glycol n-butyl-tert-butyl ether (=DGBB)
112.2 g (1.8 moles) potassium hydroxide, technical grade (about 90% strength)
248.1 g (=2 moles) monochloride mixture (97.2% strength) with 38.6% 2-chloro-2,3-dimethylbutane and 58.6% 1-chloro-2,3-dimethylbutane Diethylene glycol n-butyl-tert-butyl ether and potassium hydroxide are charged into the apparatus and heated to 200° C. under agitation and a nitrogen atmosphere, thus producing two liquid phases. Then monochloride mixture is added dropwise within 2¾ hours. After adding about 30 ml of the chlorine compound, a distillate is obtained at about 50° C. The ratio of reflux to discharge is set at 5:1. The low-boiling compounds formed are removed by distillation as set out in the table below, the first fraction being complete after 3.5 hours. Then 133 mbar is set (see the table), and the second fraction is withdrawn. Total duration: 5 hours.

| Fract. No. | Temperature °C. Sump | Temperature °C. Head | Weight (g) | Pressure mbar | Ratio Reflux to Discharge |
|---|---|---|---|---|---|
| 1 | 200 | 51–91 | 188 | normal | 5:1 |
| 2 | 134–177 | 49–168 | 48 | 133 | 5:1 |
| Residue | | | 439 | | |
| Cooling Trap | | | 6 | | |
| | | | 681 | | |

Fractions 1 and 2 and the cooling trap product are combined and, after phase separation, 32 g of water is removed. The composition of the mixture is shown in the following table under Product A.

The residue is vigorously stirred with 300 g of water and then the phases are separated:
Upper organic phase: 305 g
Lower aqueous phase: 432 g
The carbon content of this wastewater is 0.4%.

The upper phase is analyzed by gas chromatography; see Product B in table below:

GC Analyses:

| Chemical Compound | Product Mixture A | Product B |
|---|---|---|
| 2,3-Dimethylbutene-1 | 36.0% | — |
| 2,3-Dimethylbutene-2 | 7.6% | — |
| 2-Chloro-2,3-dimethyl-butane | 14.1% | |
| 1-Chloro-2,3-dimethyl-butane | 28.7% | |
| DGBB | 8.8% | 93.9% |
| High-Boiling Compounds | <0.1% | 5.0% |

The conversion of monochlorides is calculated from the above data to be 63.0%. Based on converted monochlorides, the yield of 2,3-dimethylbutene-1 is 71.1% and of 2,3-dimethylbutene-2 is 15.1%, i.e. the desired α-olefin is produced in a surprisingly high yield.

The product mixture A yields the olefins, after redistillation, in more than 98% purity according to analysis by gas chromatography.

EXAMPLE 11

The process is conducted as in Example 1, using in place of potassium hydroxide a mixture of 1 mole of potassium hydroxide and 1 mole of sodium hydroxide, as well as 2 moles of monochloride mixture having the same composition as in Example 1. A conversion of chlorine compound of 47% is attained in this method. The yields of 2,3-dimethylbutene-1 are 68.0% and 2,3-dimethylbutene-2 12.0%.

EXAMPLE 12

The process is conducted as in Example 1, using in place of DGBB n-butyl diglycol and in place of potassium hydroxide sodium hydroxide, technical grade.

490 g (=4 moles) monochloride mixture (with 32.9% 2-chloro-2,3-dimethylbutane and 65.6% 1-chloro-2,3-dimethylbutane)
80 g (=2 moles) sodium hydroxide, technical grade
240 g n-butyl diglycol The reaction temperature is set at 170° C. Here again, two liquid, readily stirrable phases are formed.

The carbon content of the wastewater is 0.1%.

The oil phase obtained after the reaction and the water scrubbing step shows, inter alia, the following composition:
n-butyl diglycol: 54.0%
diglycol n-butyl-2,3-dimethylbutyl ether: 36.4%
high-boiling compounds: 4.9%

The conversion of monochlorides is about 55%, and the yields, based on converted chlorine compounds, are:
2,3-dimethylbutene-1: 65.7 mol-%
2,3-dimethylbutene-2: 20.8 mol-%
diglycol n-butyl-2,3-dimethylbutyl ether: 12.4 mol-% (=DGBDB)

By distillation, DGBDB with a boiling point of 134° C. is obtained at 13 mbar with a purity of 98.9%.

The H-NMR spectrum of this novel ether shows three different groups of signals, corresponding to the types of protons characterized by a, b, and c in the structural formula:

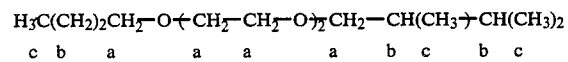

a—proton signal at 3.2–3.8 ppm
b—proton signal at 1.3–1.8 ppm
c—proton signal at 0.8–1.9 ppm measured in deuterochloroform against tetramethylsilane as the standard.

Density: d 20/4=0.8809
Index of refraction: $n_D^{20}$=1.4299
IR Bands: 740 cm$^{-1}$ (n-butyl group), 1,100–1,170 cm$^{-1}$ (R—O—R—group), 1,350–1,400 cm$^{-1}$ (CH$_3$-group).

EXAMPLE 13

The process is conducted as disclosed in Example 3, but using n-butyl triglycol instead of n-butyl diglycol. The following results are obtained:

The carbon content of the wastewater is 1.8%.

The conversion of monochloride mixture is 56.0% and the yields are:
2,3-dimethylbutene-1: 64.5 mol-%
2,3-dimethylbutene-2: 26.4 mol-%
triglycol n-butyl-2,3-dimethylbutyl ether: 6.5 mol-%

This novel ether, the boiling point of which at 13 mbar is 170°–172° C., is purified by distillation.

The position of the proton signals in the H-NMR spectrum coincides well with the DGBDB spectrum (Example 3).

Density: d 20/4=0.9301
Index of refraction: $n_D^{20}$=1.4362
IR Bands: 740 cm$^{-1}$ (n-butyl group) 1,100–1,170 cm$^{-1}$ (R—O—R—group) 1,350–1,400 cm$^{-1}$ (CH$_3$-group)

EXAMPLE 14

The process is carried out as described in Example 3, but using n-butyl glycol in place of n-butyl diglycol. Due to the relatively low boiling point, the lowermost portion of the distillation column is air-cooled. Similar results are obtained as in Examples 3 and 4.

The carbon content in the wastewater is 0.9%.

The thus-produced novel glycol n-butyl-2,3-dimethylbutyl ether has, at 13 mbar, a boiling point of 100°–103° C. and is obtained in 98% purity by distillation.

The position of the proton signals in the H-NMR spectrum of this ether coincides well with the DGBDB spectrum (Example 3).

Density: d 20/4=0.8414
Index of refraction: $n_D^{20}$=1.4218
IR Bands: 740 cm$^{-1}$ (n-butyl group), 1,100–1,160 cm$^{-1}$ (R—O—R—group), 1,350–1,400 cm$^{-1}$ (CH$_3$-group).

EXAMPLE 15

The apparatus of Example 1 is utilized, using:
245.0 g (=2 moles) monochloride mixture (with 32.9% 2-chloro-2,3-dimethylbutane and 65.6% 1-chloro-2,3-dimethylbutane)
124.7 g (=2 moles) potassium hydroxide, technical grade (about 90% strength)
336.6 g diglycol n-butyl-2,3-dimethylbutyl ether (=DGBDB)

DGBDB and potassium hydroxide are charged into the reactor and heated to 200° C. under agitation and nitrogen atmosphere. Starting with about 150° C., two liquid, readily stirrable phases are formed. The further process and the working-up operation are conducted as described in Example 1.

The following result is obtained:
The wastewater carbon content is 1.1%.
Conversion of monochloride mixture: 66%.
Yields, based on converted monochloride mixture:
2,3-dimethylbutene-1: 65.2 mol-%
2,3-dimethylbutene-2: 22.5 mol-%

EXAMPLE 16

The process is carried out as in Example 6, but adding 25 g of n-butyl diglycol to the monochloride mixture. The thus-obtained wastewater has a carbon content of 0.9%.

The following result is obtained:
Conversion of monochloride mixture: 68%.
Yields, based on converted monochloride mixture:
2,3-dimethylbutene-1: 67.3 mol-%
2,3-dimethylbutene-2: 21.1 mol-%
DGBDB: 5.0 mol-%

If mechanical losses of DGBDB occur in an industrial installation, they can be compensated for in this way by new formation of DGBDB.

EXAMPLE 17

The procedure of Example 6 is followed, except that the temperature is raised from 200° to 220° C.
Results:
The wastewater carbon content is 1.4%.
Conversion of monochloride mixture: 71%.
Yields, based on converted monochloride mixture:
2,3-dimethylbutene-1: 58.1 mol-%
2,3-dimethylbutene-2: 15.2 mol-%

EXAMPLE 18

The process is conducted as in Example 8, but the temperature is raised from 220° to 250° C.
The following result is achieved:
The wastewater carbon content is 1.8%.
The distillation residue contains about 1.2% n-butyl diglycol which has been formed by decomposition of DGBDB.
Conversion of monochloride mixture: 65%.
Yields, based on converted monochloride mixture:
2,3-dimethylbutene-1: 52.3 mol-%
2,3-dimethylbutene-2: 11.8 mol-%

EXAMPLE 19

The apparatus described in Example 1 is employed, using a crude, black product mixture which has remained in the sump of the column during the chlorination of 2,3-dimethylbutane after removal of the monochloride compounds by distillation, and which consists primarily of dichlorides of 2,3-dimethylbutane. Accordingly, the chlorine content is 42.1% as contrasted to the theoretical value of 45.7%. On account of the large number of components, an analysis of this crude product by gas chromatography cannot be fully evaluated; analysis shows a monochloride content of less than 1%.

The following compounds are utilized for dehydrochlorination:
273.0 g crude dichloro-2,3-dimethylbutane (chlorine content 42.1%)
274.3 g (=4.4 moles) potassium hydroxide, technical grade (90% strength)
1,097 g DGBDB A reaction temperature is set of 200° C. The process is further carried out as described in Example 1.

The wastewater carbon content is 1.1%.

The yield of 2,3-dimethylbutadiene is 41.9%, based on the raw material employed.

By distillation, 2,3-dimethylbutadiene is obtained in over 97% purity.

EXAMPLE 20

As demonstrated by Example 1, 1-chloro-2,3-dimethylbutane is enriched in the unreacted monochloride mixture after dehydrochlorination as compared with 2-chloro-2,3-dimethylbutane. If the unreacted monochloride mixture is repeatedly utilized in the reaction with the alkali hydroxide, pure 1-chloro-2,3-dimethylbutane is finally obtained after additional purification by distillation. The dehydrochlorination of this primary chlorine compound takes place, for example, as described in Example 3.

The following compounds are used:

110 g (=0.90 mole) 1-chloro-2,3-dimethylbutane, 98.5% strength, with 0.4% 2-chloro-2,3-dimethylbutane 56.2 g (=0.90 mole) potassium hydroxide, technical grade (about 90% strength)

224.8 g n-butyl diglycol

The following result is obtained:
The carbon content of the wastewater is 0.8%.
Conversion of monochloride mixture: 85.8%.
Yields, based on converted monochloride mixture:
  2,3-dimethylbutene-1: 60.4 mol-%
  2,3-dimethylbutene-2: 0.5 mol-%
  DGBDB: 36.6 mol-%

Thus, only minor amounts of 2,3-dimethylbutene-2 are produced from the primary chlorine compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In the dehydrochlorination of at least one of 1-chloro-3,3-dimethylbutane, 2-chloro-2,3-dimethylbutane, 1-chloro-2,3-dimethylbutane and dichloro-2,3-dimethylbutane, in an organic solvent wherein an alkali metal hydroxide is reacted with resultant hydrogen chloride to form an alkali metal chloride and water, the improvement comprising conducting said dehydrochlorination in the presence of a glycol and/or polyglycol ether of the Formula 1 and/or 2 as the solvent:

$$R_1(OCH_2CH_2)_nOR_2 \quad \text{(FORMULA 1)}$$
$$R_1(OCH_2CH_2)_nOH \quad \text{(FORMULA 2)}$$

n = 1,2,3
$R_1$ = n-butyl
  n-hexyl
  n-octyl
  2-ethylhexyl
$R_2$ = tert-butyl
  3,3-dimethylbutyl or 2,3-dimethylbutyl, so as to form a reaction mixture comprising an aqueous phase containing the alkali metal chloride and an organic phase essentially free of the alkali metal chloride, whereby the alkali metal chloride is easily removed from the reaction mixture.

2. A process according to claim 1, conducted at 100°–250° C.

3. In a process for the dehydrochlorination of a chlorinated hydrocarbon to form at least one double bond in said hydrocarbon, in an organic solvent wherein an alkali metal hydroxide is reacted with resultant hydrogen chloride to form an alkali metal chloride and water, the improvement which comprises conducting said dehydrochlorination in the presence of a glycol and/or polyglycol ether of the Formula 1 and/or 2 as the solvent:

$$R_1(OCH_2CH_2)_nOR_2 \quad \text{(FORMULA 1)}$$
$$R_1(OCH_2CH_2)_nOH \quad \text{(FORMULA 2)}$$

n = 1,2,3
$R_1$ = n-butyl
  n-hexyl
  n-octyl
  2-ethylhexyl
$R_2$ = tert-butyl
  3,3-dimethylbutyl or 2,3-dimethylbutyl, so as to form a reaction mixture comprising an aqueous phase containing the alkali metal chloride and an organic phase essentially free of the alkali metal chloride, whereby the alkali metal chloride is easily removed from the reaction mixture.

4. A process according to claim 3, conducted in the presence of an ether of Formula 1.

5. A process according to claim 3, wherein the chlorinated hydrocarbon is a chlorinated alkane.

6. A process according to claim 1, conducted in the presence of an ether of formula 2.

7. A process according to claim 3, conducted in the presence of an ether of formula 2.

8. A process according to claim 1, said dehydrochlorination being conducted in the presence of an alkali hydroxide which forms an alkali halide during the process, and further comprising washing the resultant product with water to remove said alkali chloride, and wherein said glycol and/or polyglycol ether is soluble in water to the extent of not more than 50 g/l at 20° C.

9. A process according to claim 8, wherein said glycol or polyglycol ether is soluble in water to the extent of not more than 0.5 g/l at 20° C.

10. A process according to claim 9, wherein during the dehydrochlorination, the reaction mixture is continuously distilled to remove water formed during the reaction.

11. In the dehydrochlorination of at least one of 1-chloro-3,3-dimethylbutane, 2-chloro-2,3-dimethylbutane, 1-chloro-2,3-dimethylbutane and dichloro-2,3-dimethylbutane in an organic solvent wherein an alkali metal hydroxide is reacted with resultant hydrogen chloride to form an alkali metal chloride and water, the improvement comprising conducting said dehydrochlorination in the presence of a glycol and/or polyglycol ether of Formula 1 as the solvent:

| $R_1(OCH_2CH_2)_nOR_2$ (FORMULA 1) |
|---|
| n = 1,2,3 |
| $R_1$ = n-butyl |
|   n-hexyl |
|   n-octyl |
|   2-ethylhexyl |
| $R_2$ = tert-butyl |
|   3,3-dimethylbutyl | or 2,3-dimethylbutyl, so as to form a reaction mixture comprising an aqueous phase containing the alkali metal chloride and an organic phase essentially free of the alkali metal chloride, whereby the alkali metal chloride is easily removed from the reaction mixture.

12. A process according to claim 11, wherein $R_1$ is n-butyl.

13. A process according to claim 11, wherein $R_2$ is 3,3-dimethylbutyl or 2,3-dimethylbutyl.

14. A process according to claim 11, wherein the ether is glycol n-butyl-3,3-dimethylbutyl ether, glycol n-butyl-2,3-dimethylbutyl ether, diglycol n-butyl-3,3-dimethylbutyl ether, diglycol n-butyl-2,3-dimethylbutyl ether, diglycol n-butyl-tert-butyl ether, triglycol n-butyl-3,3-dimethylbutyl ether, or triglycol n-butyl 2,3-dimethylbutyl ether.

15. A process according to claim 6, wherein n=1.

16. A process according to claim 6, wherein n=2.

17. A process according to claim 6, wherein n=3.

18. A process according to claim 15, wherein $R_1$ is n-butyl.

19. A process according to claim 15, wherein $R_1$ is n-hexyl, n-octyl, or 2-ethylhexyl.

20. A process according to claim 6, wherein the ether is n-hexyl glycol, n-octyl glycol, 2-ethylhexyl glycol, n-hexyl diglycol, n-octyl diglycol, 2-ethylhexyl diglycol, n-butyl triglycol, n-hexyl triglycol, n-octyl triglycol, or 2-ethylhexyl triglycol.

21. A process according to claim 7, wherein n=1.

22. A process according to claim 7, wherein n=2.

23. A process according to claim 7, wherein n=3.

24. A process according to claim 20, wherein $R_1$ is n-butyl.

25. A process according to claim 20, wherein $R_1$ is n-hexyl, n-octyl, or 2-ethylhexyl.

26. A process according to claim 7, wherein the ether is n-hexyl glycol, n-octyl glycol, 2-ethylhexyl glycol, n-hexyl diglycol, n-octyl diglycol, 2-ethylhexyl diglycol, n-butyl triglycol, n-hexyl triglycol, n-octyl triglycol, or 2-ethylhexyl triglycol.

* * * * *